United States Patent
Ross et al.

(10) Patent No.: US 11,461,898 B2
(45) Date of Patent: Oct. 4, 2022

(54) MEDICAL IMAGING DEVICE

(71) Applicant: OPTOS PLC, Dunfermline (GB)

(72) Inventors: Paul Ross, Dunfermline (GB); Alistair Gorman, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 112 days.

(21) Appl. No.: 16/837,650

(22) Filed: Apr. 1, 2020

(65) Prior Publication Data
US 2020/0320707 A1    Oct. 8, 2020

(30) Foreign Application Priority Data
Apr. 4, 2019 (EP) .................................... 19167393

(51) Int. Cl.
*G06T 7/00* (2017.01)
*G06T 7/262* (2017.01)
(Continued)

(52) U.S. Cl.
CPC ............ *G06T 7/0014* (2013.01); *A61B 3/102* (2013.01); *G06T 7/262* (2017.01); *G06T 7/32* (2017.01);
(Continued)

(58) Field of Classification Search
CPC ......... G06T 7/0014; G06T 7/262; G06T 7/38; G06T 2207/10101; G06T 2207/30041;
(Continued)

(56) References Cited

U.S. PATENT DOCUMENTS

2017/0140560 A1* 5/2017 Kraus .................... G06T 7/248
2019/0059723 A1   2/2019 Ono

FOREIGN PATENT DOCUMENTS

JP    2017-18202 A     1/2017
JP    2017-196210 A   11/2017
(Continued)

OTHER PUBLICATIONS

Sang, X., Lupini, A.R., Unocic, R.R., Chi, M., Borisevich, A.Y., Kalinin, S.V., Endeve, E., Archibald, R.K. and Jesse, S., 2016. Dynamic scan control in STEM: spiral scans. Advanced Structural and Chemical Imaging, 2(1), pp. 1-8.*
Mani, V.R.S. and Arivazhagan, S., 2013. Survey of medical image registration. Journal of Biomedical Engineering and Technology, 1(2), pp. 8-25.*
Maintz, J.A. and Viergever, M.A., 1998. A survey of medical image registration. Medical image analysis, 2(1), pp. 1-36 (Maintz).*
(Continued)

*Primary Examiner* — Zhitong Chen
(74) *Attorney, Agent, or Firm* — DeLucia, Mlynar & Associates LLP

(57) ABSTRACT

A medical imaging device comprising: an optical imaging module which generates an image of a region of a body part by acquiring image samples at respective sample locations in the region and mapping the samples to corresponding image pixels; a control module which controls the optical imaging module to acquire a first sequence of samples whose corresponding pixel locations follow a path which is spanned by pixels corresponding to the first sequence of samples and extends over a greater portion of the image than an arrangement in an array of a sequence of pixels corresponding to a second sequence of samples that the optical imaging module is operable to acquire, wherein a sum of distances between adjacent pixels in the sequence of pixels is equal to a length of the path; and a registration module which registers the image against a reference image.

14 Claims, 9 Drawing Sheets

(51) Int. Cl.
*G06T 7/38* (2017.01)
*A61B 3/10* (2006.01)
*G06T 7/33* (2017.01)
*G06T 7/32* (2017.01)

(52) U.S. Cl.
CPC ............... *G06T 7/337* (2017.01); *G06T 7/38* (2017.01); *G06T 2207/10101* (2013.01); *G06T 2207/30041* (2013.01)

(58) Field of Classification Search
CPC .. G06T 7/337; G06T 7/32; G06T 7/33; A61B 3/102
See application file for complete search history.

(56) References Cited

FOREIGN PATENT DOCUMENTS

| | | |
|---|---|---|
| JP | 2019-41841 A | 3/2019 |
| WO | 2015182633 A1 | 12/2015 |

OTHER PUBLICATIONS

Communication and European Search Report dated Jun. 13, 2019 issued in European patent application No. 19 167 393.8. (10 pages).
Padfield et al., "Masked Object Registration in the Fourier Domain", IEEE Transactions on Image Processing, vol. 21, Issue 5 (13 pages) (May 2012).
D. Chang, "Fingerprint recognition through circular sampling", RIT Scholar Works, Thesis/Dissertation Collections (May 1999), (31 sheets).
S. Krig, "Local Feature Design Concepts, Classification, and Learning", Computer Vision Metrics, Survey, Taxonomy, and Analysis, pp. 131-189 (2014).
Zhang Li t al., "Multi-modal and multi-vendor retina image registration", Biomedical Optics Express, vol. 9, No. 2, pp. 410-422 (2018).
Notice of Reasons for Rejection issued by the Japan Patent Office in Japanese patent application No. 2020-068564 dated Apr. 27, 2021 (English Machine translation attached).
Bro-Nielsen et al., "Fast Fluid Registration of Medical Images, Visualization in Biomedical Computing", Lecture Notes in Computer Science 1996; 1131:267-76 (1996) (10 sheets).

* cited by examiner

MEDICAL IMAGING DEVICE

This application claims the benefit of priority of European Patent Application No. 19 167 393.8, filed Apr. 4, 2019, the entire contents of which are incorporated by reference as if set forth fully herein.

FIELD

Example aspects herein generally relate to the field of medical imaging and, more particularly, to the acquisition of image data defining an image of a body part and the registration of the image against a reference image to yield data that is useful for a variety of different purposes, including feature tracking, imaging stabilization and the like.

BACKGROUND

A variety of medical imaging devices are known to acquire images of a region of a body part by performing a scan of the region in accordance with a raster scan pattern, for example, and registering the acquired images against a reference image to generate registration information for use in feature tracking, imaging stabilisation and the like.

There is, however, a need for such medical imaging devices to be capable of reliably performing the image registration operations at a higher speed for a given image data acquisition rate, relative to known devices.

SUMMARY

The present inventors have devised, in accordance with a first example aspect herein, a medical imaging device comprising an optical imaging module which is operable to generate image data defining an image of a region of a body part by acquiring samples whose values are indicative of an optical property of the body part at respective sample locations in the region and using a mapping to map the acquired samples to corresponding pixels of the image such that an indication of the sample location of each sample is mapped to a pixel location of a corresponding pixel of the image. The medical imaging device further comprises a control module configured to control the optical imaging module to generate the image data by acquiring a first sequence of samples whose corresponding pixel locations in the image follow a path that is spanned by pixels corresponding to the first sequence of samples and extends over a greater portion of the image than an arrangement in an array of a sequence of pixels corresponding to a second sequence of samples that the optical imaging module is operable to acquire, wherein a sum of distances between adjacent pixels in the sequence of pixels is equal to the length of the path. The medical imaging device further comprises a registration module configured to register the image against a reference image comprising an image of a part of the region.

The present inventors have also devised, in accordance with a second example aspect herein, a method performed by a processor of a medical imaging device comprising an optical imaging module which is operable to generate image data defining an image of a region of a body part by acquiring samples whose values are indicative of an optical property of the body part at respective sample locations in the region and using a mapping to map the acquired samples to corresponding pixels of the image such that an indication of the sample location of each sample is mapped to a pixel location of a corresponding pixel of the image. The method comprises controlling the optical imaging module to generate the image data by acquiring a first sequence of samples whose corresponding pixel locations in the image follow a path that is spanned by pixels corresponding to the first sequence of samples and extends over a greater portion of the image than an arrangement in an array of a sequence of pixels corresponding to a second sequence of samples that the optical imaging module is operable to acquire, wherein a sum of distances between adjacent pixels in the sequence of pixels is equal to the length of the path. The method further comprises registering the image against a reference image comprising an image of a part of the region.

The present inventors have further devised, in accordance with a third example aspect herein, a computer program which, when executed by a processor of a medical imaging device which further comprises an optical imaging module operable to generate image data defining an image of a region of a body part by acquiring samples whose values are indicative of an optical property of the body part at respective sample locations in the region and mapping the acquired samples to corresponding pixels of the image such that an indication of the sample location of each sample is mapped to a pixel location of a corresponding pixel of the image, causes the processor to perform a method according to the second example aspect herein.

The present inventors have further devised, in accordance with a fourth example aspect herein, a non-transitory computer-readable storage medium storing the computer program according to the third example aspect herein.

BRIEF DESCRIPTION OF THE DRAWINGS

Example embodiments herein will now be explained in detail, by way of non-limiting example only, with reference to the accompanying figures described below. Like reference numerals appearing in different figures can denote identical or functionally similar elements, unless indicated otherwise.

DETAILED DESCRIPTION OF EMBODIMENTS

Example embodiments herein will now be described in detail with reference to the accompanying drawings.

Embodiment 1

Figure 1:
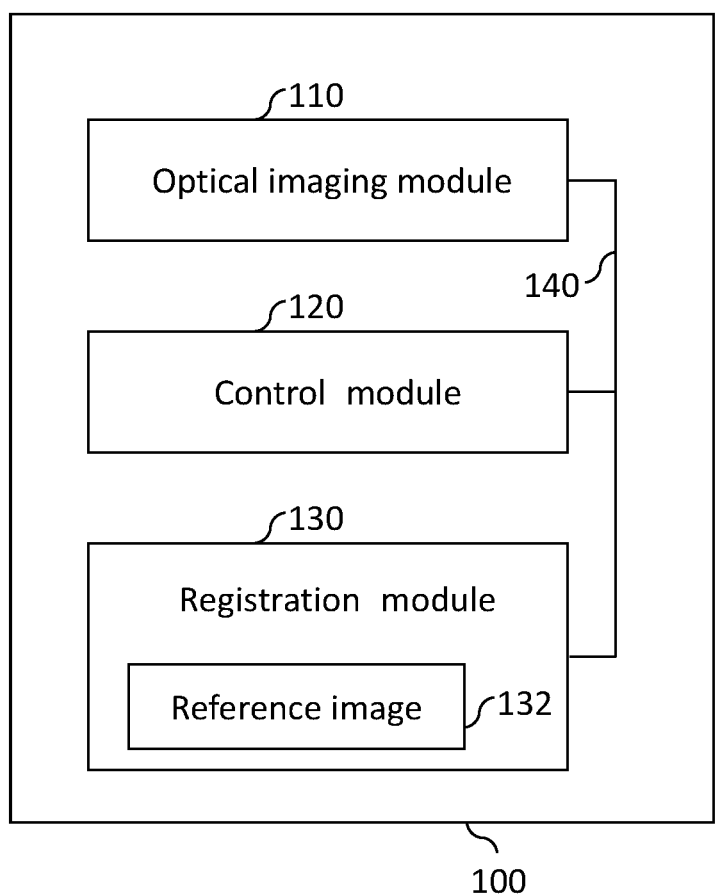
FIG. 1 is a schematic illustration of a medical imaging device according to a first example embodiment herein.

FIG. 1 is a schematic illustration of a medical imaging device 100 according to a first example embodiment.

The medical imaging device 100 of the present example embodiment comprises an optical imaging module 110, a control module 120, and a registration module 130. The optical imaging module 110, the control module 120, and the registration module 130 are communicatively coupled by any appropriate communication channel 140 (such as a data bus or the like) so as to be capable of exchanging data with one another, as described in more detail below.

The optical imaging module 110 can be any kind of optical imaging apparatus that is operable to generate image data defining an image of a region of any part of a human or animal body (the region being either on an external surface of the body part, or an internal section of the body part), by firstly acquiring samples whose values are indicative of an optical property of the body part at the respective sample locations in the region. By way of an example, the optical imaging module 110 may comprise an image sensor (such as a charge-coupled device (CCD) or complementary MOS (CMOS) sensor, for example) or more generally any kind of photodetector capable of generating image data by measuring an intensity of light transmitted through the body part, or reflected from the imaged region of the body part, or light derived from the transmitted/reflected light, such as light resulting from an interference of the transmitted/reflected light with a reference light signal, for example, at a plurality of sample locations. The sample values acquired by the optical imaging device 110 may be indicative of at least one optical property of the body part, such as its reflectance, transmittance, fluorescence or other form of photoluminescence, and/or colour, for example.

The image data generated by the optical imaging module 110 can be any numerical representation of the image derived from the acquired samples, such as bitmap image defined by an array of pixels whose locations in the array and values are indicative of the acquired sample values and sample locations, respectively. The optical imaging module 110 uses a mapping to map the acquired samples to corresponding pixels of the image such that an indication of the sample location of each sample is mapped to a pixel location of a corresponding pixel of the image. The sample value of each sample may be assigned or otherwise mapped to a pixel value of a corresponding pixel of the image. As the size of the generated image data is relatively small owing to the sparseness of the samples acquired by the optical imaging module 110 (as discussed below), the generated bitmap image may, as in the present example embodiment, preferably be stored, without compression, in a raw format (e.g. as the raw bitmap, without a header or other information such as size information) in a memory device of the optical imaging module 110, for increased processing speed. The generated bitmap image may, however, alternatively be stored in the memory device in any known compressed image file format, for example in a standardized compressed bitmap file such as GIF, PNG, TIFF or JPEG.

The medical imaging device 100 may be provided in one of many different forms. By way of an example, the medical imaging device 100 of the present example embodiment is provided in the form of a retinal scanner for imaging a region of the retina of a patient's eye. It should be understood, however, that the configurational and operational aspects of the retinal scanner described in the following are not necessarily particular to retinal scanners and can be applicable to other kinds of medical scanner and medical imaging devices.

The retinal scanner may, as in the present example embodiment, be a scanning laser ophthalmoscope (SLO) for imaging the surface of the retina. The retinal scanner may, for example, take the form of a wide-field SLO having an optical arrangement as described, for example, in U.S. Pat. No. 5,815,242, the contents of which are incorporated herein by reference in their entirety, or alternatively a narrower-field SLO of a conventional type well-known to those versed in the art. The retinal scanner may alternatively be one of a number of known optical coherence tomography (OCT) scanners that are configured to acquire OCT image data defining an image of a region of the retina at a prescribed depth beneath its surface. As a further alternative, the retinal scanner may be a combined SLO-OCT scanner, which is capable of acquiring both a confocal fundus image via SLO optics and a tomographic image via OCT optics in a single procedure. An example of a wide-field combined SLO-OCT scanner is described in U.S. Pat. No. 9,924,862, the contents of which are incorporated herein by reference in their entirety.

The retinal scanner may image the region by scanning a collimated beam of light along the region and measuring, for each sample location of a sequence of sample locations on the region covered by the scan, the intensity of light reflected from the respective sample location using an image sensor or other photodetector arrangement that is capable of measuring the intensity of the reflected light, thus obtaining a sequence of samples of the intensity of the reflected light. For each acquired sample, the retinal scanner forms an association (for example, by storage in an appropriately configured data structure, which may be visualised as a table or the like) between the sample value and the values of one or more scan parameters (for example, one or more control signals for controlling the angular displacement of one or more scanning elements of the retinal scanner) that are indicative of the corresponding sample location.

As an example, in an embodiment where the retinal scanner comprises a first and a second scanning element that are provided in an optical arrangement as described in European patent EP 0 730 428 B1 so as to allow collimated light to be scanned across the retina by control of their rotations, the retinal scanner may form an association between the measurement result, $R_i$, of each intensity measurement, i (where i=1, ... N in case of N samples being acquired in the scan), and corresponding values, $D_\theta(i)$ and $D_\phi(i)$, of drive signals, $D_\theta$ and $D_\phi$, according to which the scanning element(s) of the retinal scanner are set when the measurement i is made, the values $D_\theta(i)$ and $D_\phi(i)$ thus being indicative of the location of the measurement i on the retina.

The retinal scanner may generate the image data defining the image of the scanned region by using the aforementioned mapping to map the acquired samples to corresponding pixels of the image, such that a sample value ($R_i$ in the above example) and the indication of the sample location (e.g. $D_{74}(i)$ and $D_\phi(i)$ in the above example) of each sample are mapped to a pixel value and a pixel location of a corresponding pixel of the image. This mapping may be performed to generate the image data after the acquisition of samples has been completed and/or during sample acquisition. The mapping may be obtained on the basis of a measured or calculated response of the scan mirror(s) to the control signals and an optical model of the retinal scanner, for example, using techniques well-known to those skilled in the art.

Figure 2A:
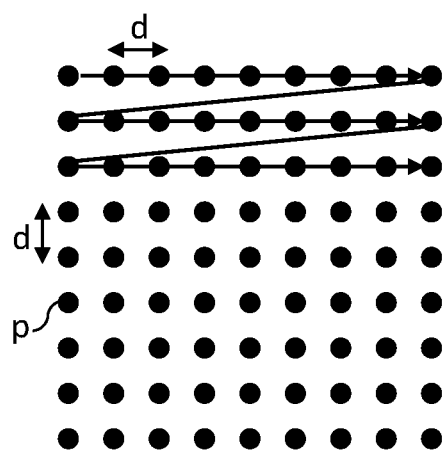
FIG. 2(a) is a schematic illustration of a sequence of pixels that are arranged in an array, in a first example image generated by an optical imaging module of the first example embodiment.

In a first mode of operation, the control module 120 may control the optical imaging module 110 to acquire a sequence of samples in accordance with a dense scan pattern, the dense scan pattern being such that, in the generation of the image data by the optical imaging module 110, sample locations on the retina of the acquired samples are mapped to corresponding pixel locations in the image that are arranged in an array. The dense scan pattern may be a raster scan pattern, in one example, in which case the sequence of acquired samples is mapped onto a corresponding sequence of pixels whose ordering reflects the ordering of the acquired samples in accordance with the raster scan pattern, as shown in the schematic illustration of the generated image in FIG. 2(a). In FIG. 2(a), the pixels p, whose pixel locations in the image are a mapping of the sample locations on the retina, are shown, by way of an example, to be arranged in rows and columns in an array (or grid), with a spacing d between adjacent pixel locations in any row or column of the array. In this example, the spacing between adjacent pixel locations in the sequence is d, with the exception of the spacing between the location of the last pixel in each row of the array and the location of the next pixel in the sequence that is in the next row of the array and on the opposite side of the array. The spacing between these adjacent pixel locations is $65^{1/2}d$, as there are 9 pixels in each row in this illustrative example.

Figure 2B:
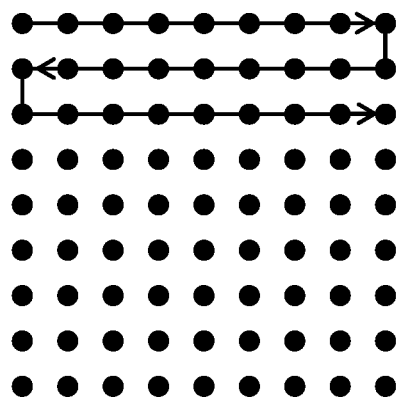
FIG. 2(b) is a schematic illustration of a sequence of pixels that are arranged in an array, in a second example image generated by an optical imaging module of the first example embodiment.

In an alternative example, in which the dense scan pattern is a 'python' or 'S' scan pattern, the pixels in the generated image are similarly arranged in an array, as illustrated in FIG. 2(b), although the spacing between the location of the last pixel in each row of the array and the location of the next pixel in the sequence, which is in the next row of the array and on the same side of the array, is d in this example (the spacing between the locations of all other adjacent pixels again being d).

Figure 2C:
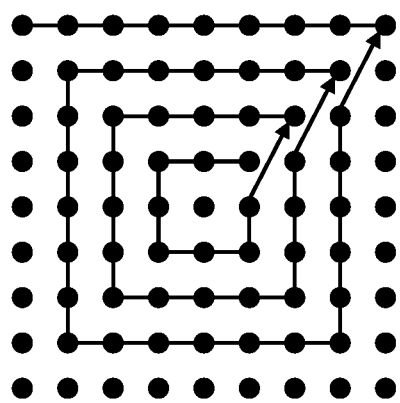
FIG. 2(c) is a schematic illustration of a sequence of pixels that are arranged in an array, in a third example image generated by an optical imaging module of the first example embodiment.

A further example of an arrangement of the image pixels in an array is shown in FIG. 2(c), in which the path followed by the sequence of pixels in the image reflects the acquisition of samples by the optical imaging module 110 in a scan pattern that partially traces a series of concentric squares, tracing most of each square before switching to trace most of the next larger square, etc.

In the first mode of operation, the control module 120 thus controls the optical imaging module 110 to perform a dense scan using a scan pattern of one of the different kinds described above, for example, thereby devoting the available scan time to the acquisition of image data defining an image of a relative small portion of the retina, with the spacing of adjacent sample points on the retina typically being similar to the optical resolution of the optical imaging module 110.

In order to achieve improved registration efficacy without requiring the speed of the retinal scanner's scanning element(s) and the sampling rate to be increased, the control module 120 is operable in a second operational mode to control the optical imaging module 110 to acquire samples using a sparse scan pattern, such that a resulting sparse image frame provides coverage of a larger overall region of the retina than an image acquired by the optical imaging module 110 when using the dense scan pattern of the first operational mode. More particularly, the control module 120 can operate in the second mode to control the optical imaging module 110 to generate image data by acquiring a first sequence of samples whose corresponding pixel locations in the image follow a path that is spanned by pixels corresponding to the first sequence of samples and extends over a greater portion of the image than an arrangement in an array of a sequence of pixels corresponding to a second sequence of samples that the optical imaging module 110 can acquire when operating in the first mode as described above, wherein a sum of distances between adjacent pixels in the sequence of pixels is equal to the length of the path.

Figure 3:
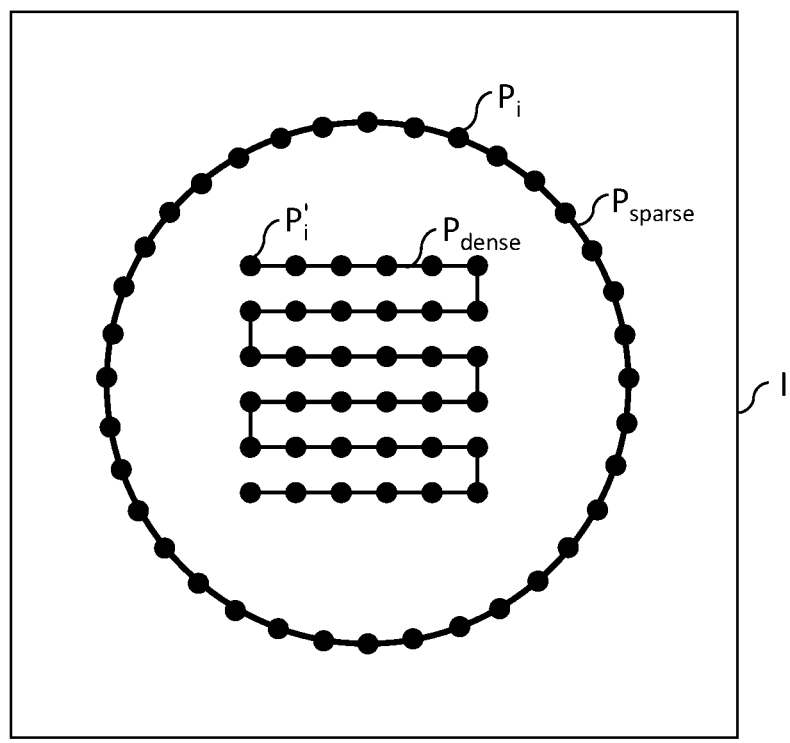
FIG. 3 is a schematic illustration of an image frame comprising a set of pixels $P_i$ arranged along a path $P_{sparse}$ corresponding to samples acquired by the optical imaging module of the first example embodiment using a spare scan pattern and, for comparison, another set of pixels $P_i'$ arranged in an array and along a second path $P_{dense}$, which correspond to samples acquired by the optical imaging module of the first example embodiment using a dense scan pattern.

In the present example embodiment, the control module 120 is configured to determine the sample locations at which optical imaging module 110 acquires the samples in the first sequence using a function which defines a circle (e.g. $(x-x_1)^2+(y-y_1)^2=r^2$, where $(x_1, y_1)$ is the centre of a circle of radius r). As illustrated in FIG. 3, the locations of pixels $P_i$ in the image frame I corresponding to the first sequence of samples acquired in the sparse scan follow a circular path $P_{sparse}$ which has a circumference that is the same as the length of path $P_{dense}$ corresponding to the sum of the distances between adjacent pixels in a sequence of pixels $P'_i$, corresponding to a second sequence of samples that the optical imaging module 110 would acquire when operating in the first mode, using a dense scan pattern as described above. As shown in FIG. 3, the circular path $P_{sparse}$ extends over a greater portion of the image frame I than the arrangement of pixels along path $P_{dense}$ in an array. The path may extend over a greater portion of the image frame I than the aforementioned array of pixels so that, for example, the largest straight-line distance in the image frame between pixels corresponding to the samples in the first sequence of samples acquired during operation of the control module 120 in the second mode is greater than the largest straight-line distance between pixels corresponding to samples in the second sequence of samples that would be acquired during operation of the control module 120 in the first mode.

Figure 4A:
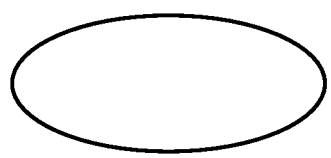
FIGS. 4(a) to 4(d) illustrate curves represented by different examples of a function which a control module may use to determine sample locations at which the optical imaging module acquires samples in the first example embodiment, with FIG. 4(a) illustrating an ellipse, FIG. 4(b) illustrating a Lissajous figure, FIG. 4(c) illustrating a hypotrochoid, and FIG. 4(d) illustrating a spiral.
Figure 4B:
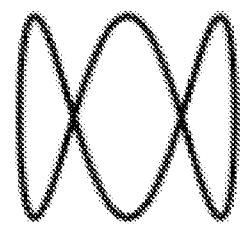
Figure 4C:
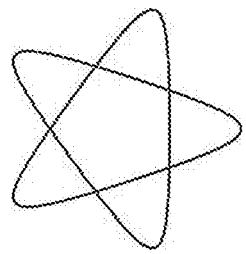
Figure 4D:
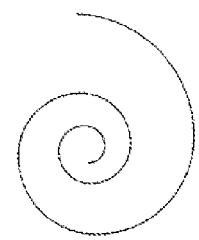

The control module 120 may alternatively be configured to determine the sample locations at which the optical imaging module 110 acquires the samples in the first sequence using a function which defines an ellipse other than a circle (e.g. $(x-x_1)^2/a^2+(y-y_1)^2/b^2=1$, where $(x_1, y_1)$ is the centre of the ellipse). More generally, the function may be any function that defines a curve in a plane. Further examples of the curve are illustrated in FIGS. 4(a) to 4(d). The curve may be a closed curve such as a non-circular ellipse (as illustrated in FIG. 4(a)), a Lissajous figure (as illustrated in FIG. 4(b)), or a hypotrochoid (as illustrated in FIG. 4(c)), for example. The curve may alternatively be an open curve such as a spiral (as illustrated in FIG. 4(d)), or a straight line, for example. In an optical imaging module comprising one or more scanning elements as described above, the control module 120 may generate control signals for driving the rotation of the scanning element(s) on the basis of the function, so that the collimated light is scanned across the retina in accordance with the sparse scan pattern defined by the function. During the scan, the optical imaging module 110 may acquire samples at a constant sampling rate, as in the present example embodiment, or at irregular intervals.

The registration module 130 is configured to register the image defined by the generated image data against a reference image 132 stored therein, which includes image data defining an image of at least a part of the region that has been imaged by the optical imaging module 110. In the present example embodiment, the area of the retina imaged in the reference image 132 is larger than the area of the retina covered by a single dense scan of the kind described above that is performed by the optical imaging module 110.

The registration module 130 may register the image against the reference image 132 by calculating a cross-correlation between the image and the reference image 132. For example, the registration module 130 may, as in the present example embodiment, be configured to register the image against the reference image 132 by calculating a Weighted Normalized Cross-correlation (in other words, a Masked Normalized Cross-correlation) between the image and the reference image 132. Further details of how the Weighted Normalized Cross-correlation calculation may be performed are provided in, for example, the article titled "Masked Object Registration in the Fourier Domain" by D. Padfield, published in IEEE Transactions on Image Processing, Vol. 21, Issue 5, pages 2706-2718, on 5 May 2012 (see the section titled "II. METHODS" in particular), the contents of which are incorporated herein by reference in their entirety. This technique allows registration of sparse image data by considering only genuine data points; non-data points in a sparse image frame are excluded from the registration computation by use of a mask. The registration module 130 of the present example embodiment is thus configured to produce a measure of a translation offset between two images. The registration module 130 may be configured to register the image directly against the reference image 132, as in the present example embodiment, or indirectly by registering image against a previously acquired image in a sequence of images acquired by the optical imaging module 110, wherein a difference of the aforementioned kind(s) between the previously acquired image and the reference image 132 is known.

In the present example embodiment, the reference image 132 used by the registration module 130 is acquired prior to the performance of the registration by the registration module 130, for example by forming a mosaic of images of adjacent imaging areas on the retina that are each imaged by the optical imaging module 110 using a dense scan pattern. The adjacent imaging areas preferably overlap in order to allow the images to be registered against each other so that they can be combined (or stitched together) to generate the mosaic of images forming the reference image 132.

The configuration of the control module 120 to control the optical imaging module 110 to generate image data using a sparse scan pattern as described above, instead of a dense scan pattern, and the configuration of the registration module 130 to register the image produced by the sparse scan against the reference image 132, may provide one or more of the following benefits: (i) it may enable high frame-rate feature tracking with a relatively low data rate and relatively low-speed scanners relative to prior art devices; (ii) for a given data rate, it may offer improved registration efficacy over non-sparse methods (as one sparse frame can provide coverage of a larger overall region of the retina than a frame produced via a dense scan pattern), allowing higher image fidelity to be achieved when the registration is used in the processing of images to compensate for movement, and more precise scanning of a specific region of interest to be achieved when the registration is used for controlling the optical imaging module 110 to maintain a 'lock' on the region of interest; and (iii) the sparse scan pattern can be constructed to intersect regions of high detail, so that registration can be performed even when acquiring data from less detailed regions, as long as the scan trajectory intersects at least one high-detail region somewhere along its path. The configuration of these components of the medical imaging device 100 may enable effective motion compensation.

The medical imaging device 100 may, as in the present example embodiment, be configured such that each incoming image frame (acquired with using the sparse scan pattern as described above) is registered against the reference image 132 to determine a translation offset and, if the offset is greater than a specific threshold, the scan pattern is re-centred to follow any movement. This may allow for a greater degree of translation offset than in known devices, whilst still remaining within range of the scan pattern.

Example aspects described herein improve medical imaging methodologies and devices for acquiring images of body parts, by virtue of providing the above-described benefits, and, for at least some embodiments, also by virtue of enabling reliable image registration operations to be performed at a higher speed for a given data acquisition rate, relative to known methods/devices. Also, by virtue of the capabilities of at least some example aspects described herein, which are rooted in computer technology, those example aspects described herein also improve computer technology by, for example and without limitation, enabling the higher speed image registration operations and associated faster computer processing to be performed, relative to known methods/devices.

Figure 5:
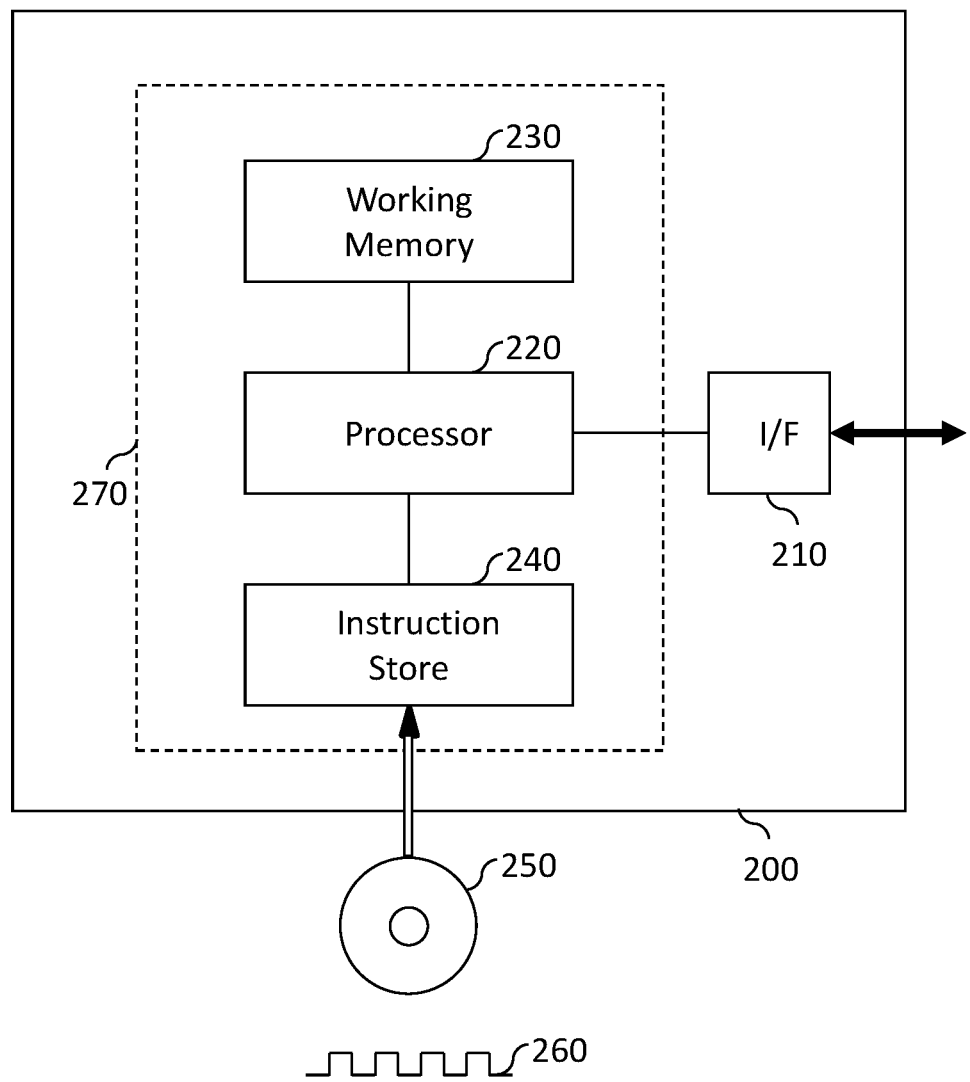
FIG. 5 is a block diagram illustrating an example signal processing hardware configuration of the control module and/or registration module of the first example embodiment.

FIG. 5 is a schematic illustration of a programmable signal processing hardware 200, which may be configured to control a medical imaging device comprising an optical imaging module 110 as described in the first example embodiment and, in particular, function as the control module 120 and/or the registration module 130 (and/or the updating module 150 of the second embodiment described below). The programmable signal processing hardware 200 comprises a communication interface (I/F) 210 for receiving sample data acquired by the optical imaging module 110, and sending control instructions to the optical imaging module 110 to control the optical imaging module 110 to acquire samples in accordance with a sparse scan pattern and, optionally, based on offsets obtained in the registration (in order to maintain the scan location on a region of interest on the retina, so as to compensate for movements of the eye during imaging). The signal processing apparatus 200 further comprises a processor (e.g. a Central Processing Unit, CPU, or Graphics Processing Unit, GPU) 220, a working memory 230 (e.g. a random access memory) and an instruction store 240 storing a computer program comprising the computer-readable instructions which, when executed by the processor 220, cause the processor 220 to perform various functions including those of the control module 120, the registration module 130 and/or the updating module 150 described herein. The working memory 230 stores information used by the processor 220 during execution of the computer program, including image data generated by the optical imaging device 110, the reference image 132, one or more offsets calculated during the image registration, one or more functions defining the scan pattern, and the candidate imaging templates described below, for example. The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions of the computer program can be input thereto from a computer program product, such as a non-transitory, computer-readable storage medium 250 in the form of a CD-ROM, DVD-ROM, etc. or a computer-readable signal 260 carrying the computer-readable instructions. In any case, the computer program, when executed by the processor, causes the processor to execute a method(s) of controlling a medical imaging device 100 as described herein, and methods shown in FIGS. 6, 8, and 9. It should be noted, however, that the control module 120, the registration module 130 and/or the updating module 150 may alternatively be implemented in non-programmable hardware, such as an application-specific integrated circuit (ASIC).

In the present example embodiment, a combination 270 of the hardware components shown in FIG. 5, comprising the processor 220, the working memory 230 and the instruction store 240, is configured to perform functions of the control module 120 and the registration module 130, and/or the functions of the updating module 150 described below.

Figure 6:
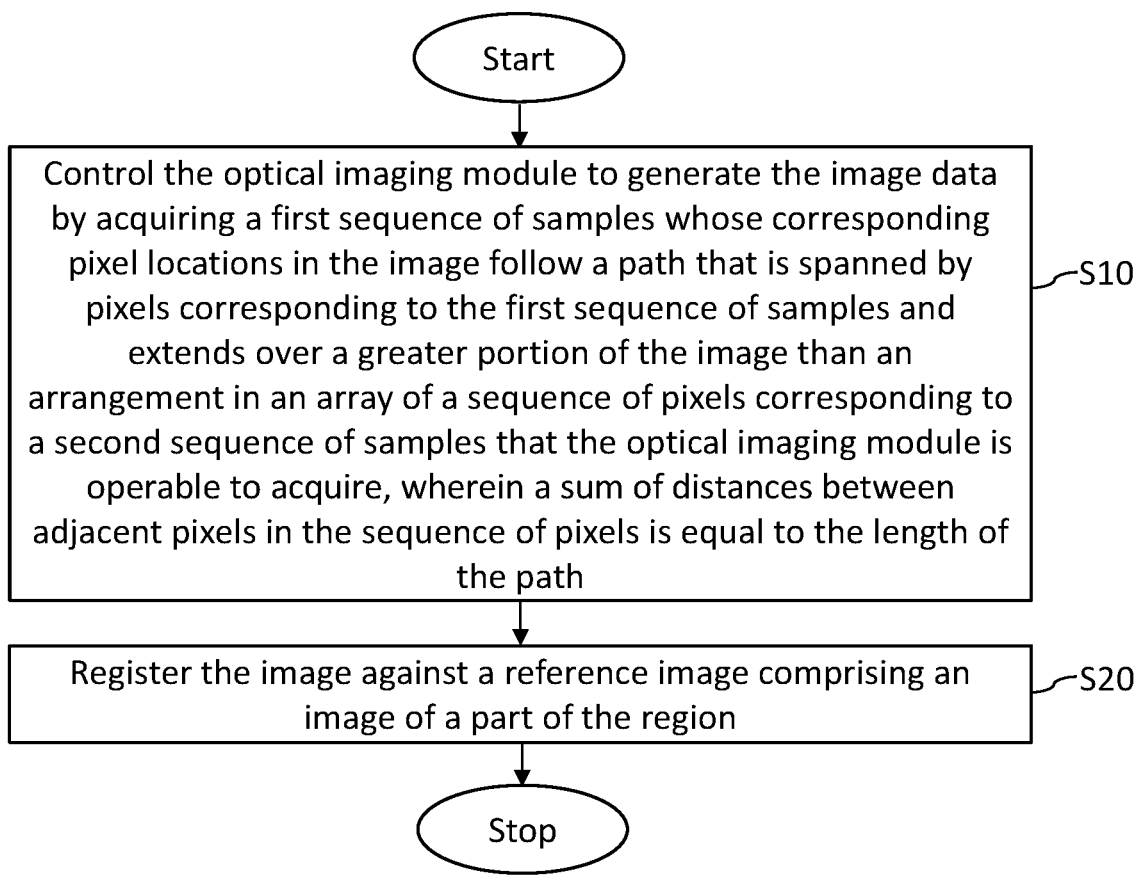
FIG. 6 is a flow diagram illustrating a method performed by a processor of FIG. 5, by which the processor controls the optical imaging module of the first example embodiment.

FIG. 6 is a flow diagram illustrating a method performed by the processor 220, by which the processor 220 controls the optical imaging module 110 to generate image data defining an image of a region of a body part, and registers the image against a reference image 132.

In step S10 of FIG. 6, the processor 220 controls the optical imaging module 110, as described above, to generate the image data by acquiring the first sequence of samples described above, whose corresponding pixel locations in the image follow a path that is spanned by pixels corresponding to the first sequence of samples and extends over a greater portion of the image than an arrangement in an array of a sequence of pixels corresponding to the second sequence of samples that the optical imaging module 110 is operable to acquire, wherein a sum of distances between adjacent pixels in the sequence of pixels is equal to the length of the path.

Then, in step S20 of FIG. 6, the processor 220 registers the image against a reference image 132 comprising an image of a part of the region, as described above.

Embodiment 2

Figure 7:
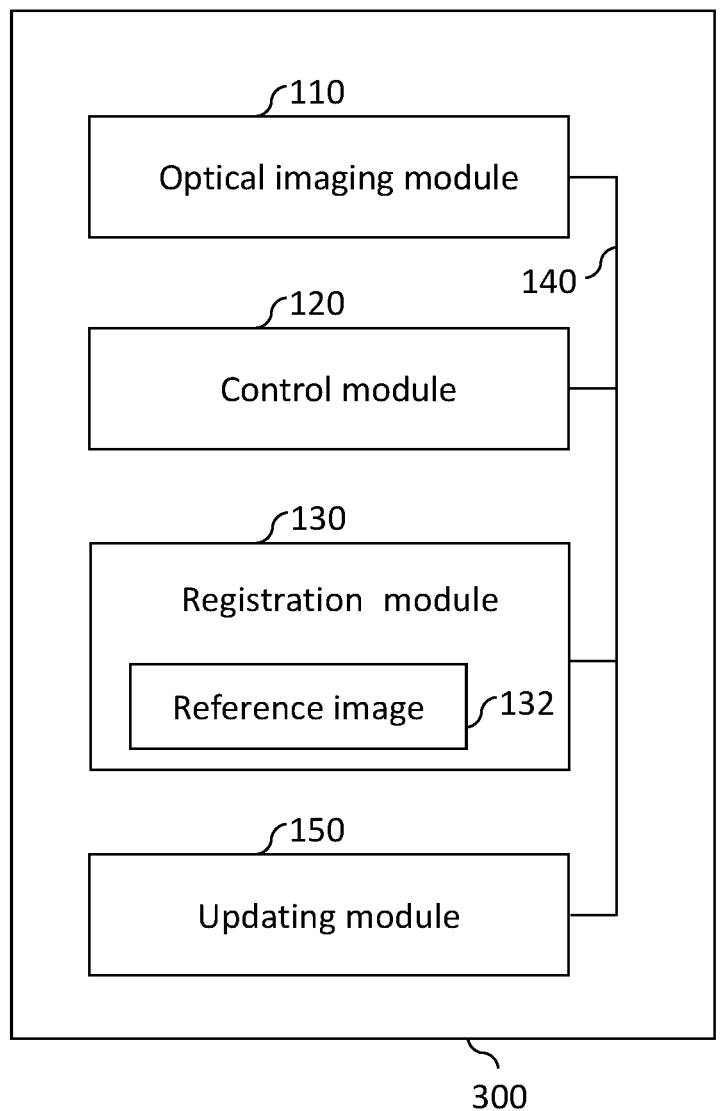
FIG. 7 is a schematic illustration of a medical imaging device according to a second example embodiment herein.

FIG. 7 is a schematic illustration of a medical imaging device 300 according to a second example embodiment.

The medical imaging device 300 of the present example embodiment comprises an optical imaging module 110, a control module 120, and a registration module 130 that are the same as in the first example embodiment, but differs from the first example embodiment by including a mechanism for constructing the reference image 132 that is used by the registration module 130 for registering the acquired sparse images. In the present example embodiment, the reference image 132 is constructed by accumulating, into an incomplete reference image, sparse image data from acquired sparse images after these images have been registered against the reference image 132, thereby increasing the reference image's area coverage. Owing to the sparse nature of the scan performed by the optical imaging module 110 under the control of the control module 120 in the second mode of operation described above, this updating mechanism may allow a relatively broad area of the reference image 132 to be populated with pixels corresponding to sample data from each sparse scan, allowing the reference image 132 to be built up to a level useable for image registration in a shorter period of time than in the first example embodiment described above, where the reference image 132 is formed as a mosaic of images that are acquired by performing a dense scan on adjoining sections of the retina. In other words, the medical imaging device 300 of the present example embodiment, with the control module 120 thereof operating only in the second mode, may reach a state in which it is capable of reliably registering images of a region of a body part, for which no prior image data exists, in a shorter period of time than the medical imaging device 100 of the first example embodiment, which generates the reference image using only dense scans as described above.

The updating module 150 of the medical imaging device 300 is configured to update the reference image 132 to include the image data of the image that has been registered against the reference image 132 in step S20 of FIG. 6, thereby generating an updated reference image 132 that includes this supplementary information.

In order to reduce the likelihood of the reference image 132 being updated to include image data of a sparse image that has not been correctly registered against the reference image (owing to an insufficient degree of overlap between retinal features imaged in the sparse image and the reference image 132) and thus degrading the quality of the reference image, the updating module 150 may, as in the present example embodiment, update the reference image 132 only if a maximum of the calculated Weighted Normalized Cross-correlation between the sparse image and the reference image 132 exceeds a predetermined threshold.

As noted above, the registration module 130 may be configured to register the acquired sparse image against the reference image 132 by determining a translational difference between the sparse image and the reference image 132. The updating of the reference image 132 by the updating module 150 may be conditional not only on the maximum of the calculated Weighted Normalized Cross-correlation between the image and the reference image 132 exceeding the threshold, but also on the determined translational difference exceeding a respective threshold. In this way, the processing overhead associated with the updating of the reference image data that does not sufficiently increase its coverage can be avoided.

In the present example embodiment, the optical imaging module 110, the control module 120, the registration module 130 and the updating module 150 are configured to perform the acquiring and mapping of the sparse samples, the registering of the sparse image against the reference image 132, and the generating of the updated reference image in an iterative process, such that the sparse image defined by the image data generated by the optical imaging module 110 in each iteration of this iterative process is registered by the registration module 130 against, and subsequently used by the updating module 150 to update, the reference image 132 updated in a previous iteration of the iterative process.

An example of this iterative process will now be described with reference to FIG. 8.

Figure 8:
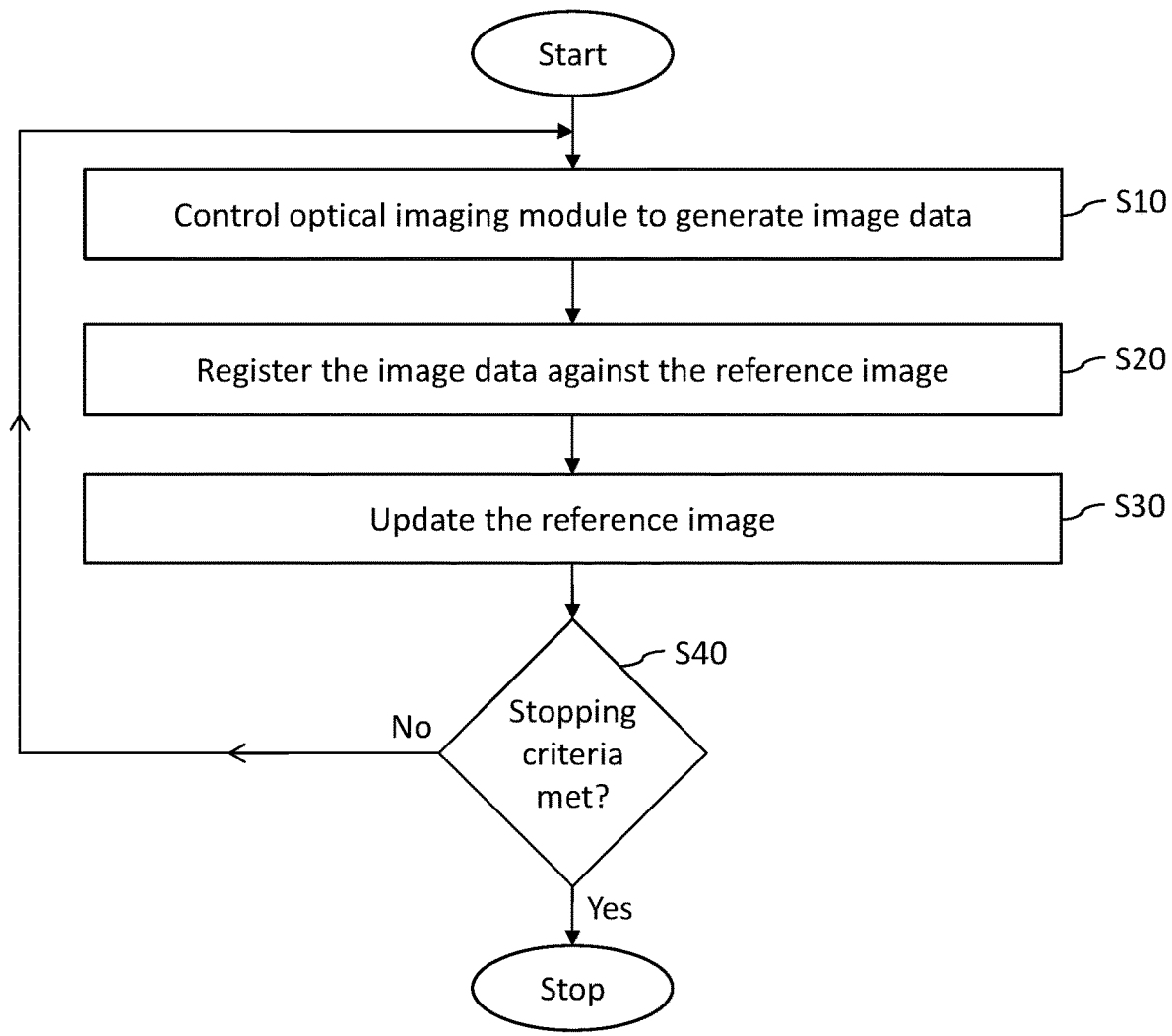
FIG. 8 is a flow diagram illustrating an iterative process by which an optical imaging module of the second example embodiment is controlled.

In each of the iterations of the iterative process shown in FIG. 8, the control module 120 and the registration module 130 perform steps S10 and S20, respectively, which are the same as in the first example embodiment described above with reference to FIG. 6. In step S30, the updating module 150 updates the reference image 132 to include the image data of the sparse image that has been registered against the reference image 132, thereby generating an updated version of the reference image 132, against which the sparse image acquired by the optical imaging module 110 in the next iteration is registered by the registration module 130 in that subsequent iteration. The updating of the reference image 132 by the updating module 150 may subject to a condition being met, as described above (i.e. a maximum of the calculated Weighted Normalized Cross-correlation between the sparse image and the reference image 132 exceeding a predetermined threshold), or it may be unconditional so that the reference image 132 is updated in each iteration. In either case, the reference image 132 used by the registration module 130 in each performance of step S20 is an updated reference image 132 that has been updated in a previous iteration. In each iteration of the process shown in FIG. 8, the control module 120 determines in step S40 whether a stopping criterion has been met, and continues to perform the iterative process by looping back to step S10 if the stopping criterion has not been met, and otherwise stops the processing if the stopping criterion has been met. The stopping criterion may, for example, be that a sufficiently dense reference image of the desired area-coverage has been constructed, as determined by a ratio of a number of different pixels in the reference whose values have been updated to the total number of pixels in the reference image 132. The stopping criterion may additionally or alternatively be that a predetermined number of iterations have been performed, or that an instruction to terminate the process has been generated by a user of the medical imaging device 300 or by an image acquisition control process (e.g. for controlling the acquisition of tomographic data on a combined SLO-OCT imaging system) being executed on the device, for example.

Thus, in each successive image frame, the sparse scan pattern covers an area which has not yet been acquired with the required quality, thus increasing the area coverage and/or quality when accumulated into the partial reference image. It is noted that that the sparse image always has regions of overlap with the accumulating reference image, thus facilitating registration with it. The process can be supplemented with image-data infill if there are missing pixels in the final reference image.

In the present example embodiment, the control module 120 is configured to control the optical imaging module 110 to acquire samples in step S10 using the same sparse scan pattern in each of the iterations of the iterative process, so as to generate image data defining a plurality of images of different respective regions of the body part that are offset relative to one another, by acquiring a plurality of sequences of the samples, wherein the pixels to which the samples of the acquired sequences of samples are mapped have pixel locations that follow the same path in each of the sparse images. Natural movements of the subject's retina relative to the optical imaging module 110 during imaging may, as in the present example embodiment, be sufficient to cause the scan location on the retina of the sparse scan performed by the optical imaging module 110 to differ from one iteration to the next, so that the sparse scan covers a different region of the retina in each iteration (although the difference in coverage from one scan to the next may not always be sufficient to trigger the updating of the reference image 132, so noted above, so that the reference image 132 may not be updated in each iteration). Such natural movements of the subject's eye are generally beyond the subject's control and may occur despite measures being taken to reduce them, such as the placement of the subject's chin on a chin rest and the like.

In a variant of the medical imaging device 300, which may be used in applications where the natural movement of the retina relative to the optical imaging module 110 on the time-scale of the image acquisition process are insignificant, the control module 120 may be configured to control the optical imaging module 110 to acquire a plurality of sequences of the samples using a different scan pattern in each of the iterations of the iterative process, so as to generate image data defining a plurality of images of the region of the body part, wherein the pixels to which the samples of the acquired sequences of samples are mapped have pixel locations that follow a different path in each of the images. In this variant, the control module 120 uses a different scan pattern in each of the iterations, thereby ensuring that a different region of the retina is covered by each scan. The scan pattern may be varied in one of a number of different ways in the iterative process, for example by systematically translating, rotating and/or scaling the sparse scan pattern by a predetermined increment(s) in each iteration, and/or varying in each iteration the function which defines the shape of the sparse scan.

A particularly advantageous method of controlling the optical imaging module 110 to generate the image data, in accordance with a second variant of the medical imaging device 300, will now be described with reference to FIG. 9, which illustrates a process by which the control module 120 of this second variant generates image data in its performance of step S10 in FIGS. 6 and 8.

In the second variant, control module 120 is configured to keep a record of a number of times each of a plurality of pixels of the reference image 132 has been updated during the performance of the iterative process. For example, the control module 120 may store a record in the form of a two-dimensional data array which has the same number of rows and columns as there are pixel rows and pixel columns in the reference image 132, and store in each cell of this data array a count value representing the number of times that the pixel at the corresponding location in the reference image 132 has been updated so far in the iterative process.

Figure 9:
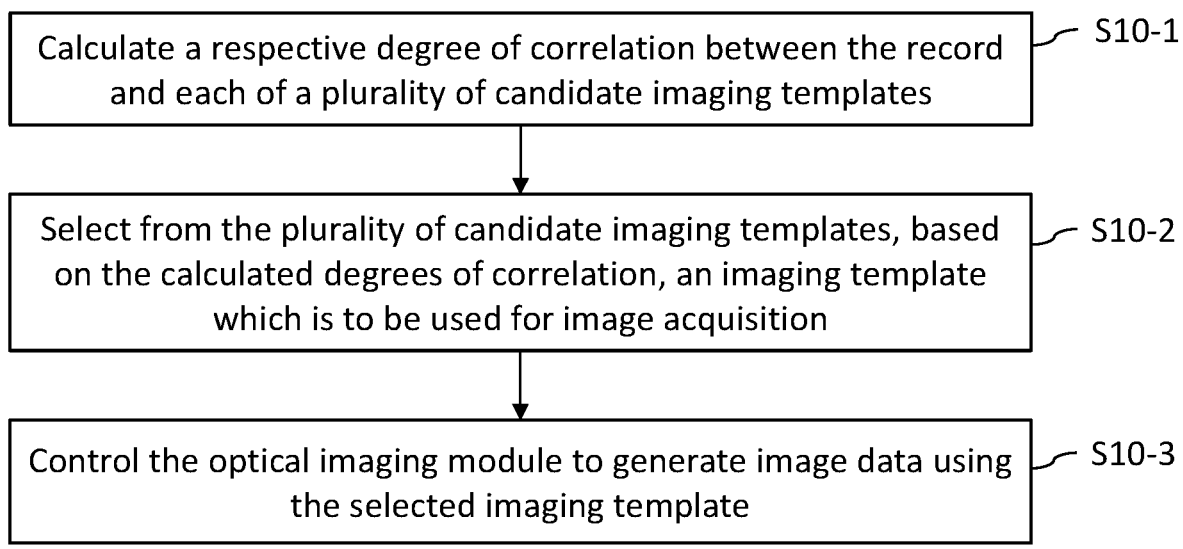
FIG. 9 is a flow diagram illustrating a method of controlling the optical imaging module to generate image data, in accordance with a variant of the second example embodiment described herein.

In each of the iteration of the iterative process, the control module 120 of the second variant calculates in step S10-1 of FIG. 9 a respective degree of correlation between the record and each of a plurality of candidate imaging templates, wherein each candidate imaging template comprises a different predicted image of a candidate region of the retina to be imaged by the optical imaging module 110. The predicted image in each imaging template may comprise pixels having a common pixel value, which are located at pixel locations in the imaging template that can be mapped to a corresponding set of optical imaging module control parameter values using a mapping of the kind described above. In the second variant, the optical imaging module 110 can be controlled by the control module 120 to generate, in accordance with each of the candidate imaging templates, image data defining an image of a respective candidate region of the body part by acquiring samples whose values are indicative of the optical property of the body part at respective sample locations in the candidate region, and mapping the acquired samples to corresponding pixels of the image such that the sample value and an indication of the sample location of each sample are mapped to a pixel value and a pixel location of a corresponding pixel of the image, wherein the optical imaging module 110 is configured to use the mapping to determine sample locations in the candidate imaging region at which the samples are to be acquired.

In step S10-2 of FIG. 9, the control module 120 selects, from the plurality of candidate imaging templates and based on the degrees of correlation that have been calculated in step S10-1, an imaging template which is to be used for image acquisition in that iteration. The control module 120 may select, as the imaging template, an imaging template from the plurality of candidate imaging templates whose calculated degree of correlation with the record is between a highest of the calculated degrees of correlation and the lowest of the calculated degrees of correlation, and preferably a median of the calculated degrees of correlation. Low values of the degree of correlation correspond to scan locations that will increase coverage of the reference image 132 at the expense of overlap between areas covered by the reference image 132 and the acquired image frame, and high values correspond to there being regions of the retina that have been sampled to a greater degree; intermediate values correspond to areas with some overlap as required for tracking and new areas of retina required to increase coverage.

Then, in step S10-3 of FIG. 9, the control module 120 controls the optical imaging module 110 to generate image data using the imaging template selected in step S10-2 of FIG. 9.

The image defined by the image data that has been generated in accordance with the selected imaging template is then registered against the reference image 132 by the registration module 130, and the updating module 150 updates the reference image 132 to include the image data of the image that has been registered against the reference image 132. In the second variant, the updating module 150 updates the record using the image data of the image that has been registered against the reference image 132, by incrementing the count in each cell of the record whose corresponding location in the reference image 132 has a pixel whose pixel value has been updated in the current iteration.

Some of the embodiments described above are summarised in the following examples E1 to E11:

E1. A method performed by a processor of a medical imaging device (100; 300), comprising an optical imaging module (110) which is operable to generate image data defining an image (I) of a region of a body part by acquiring samples whose values are indicative of an optical property of the body part at respective sample locations in the region and using a mapping to map the acquired samples to corresponding pixels of the image (I) such that an indication of the sample location of each sample is mapped to a pixel location of a corresponding pixel of the image (I), the method comprising:

controlling the optical imaging module (110) to generate the image data by acquiring a first sequence of samples whose corresponding pixel locations in the image (I) follow a path that is spanned by pixels corresponding to the first sequence of samples and extends over a greater portion of the image (I) than an arrangement in an array of a sequence of pixels corresponding to a second sequence of samples that the optical imaging module (110) is operable to acquire, wherein a sum of distances between adjacent pixels in the sequence of pixels is equal to a length of the path; and registering the image (I) against a reference image (132) comprising an image of a part of the region.

E2. The method according to E1, wherein the sample locations at which the optical imaging module (110) acquires the samples in the first sequence are determined based on a function which defines one of a spiral, an ellipse, an elliptical spiral, a Lissajous figure, and a hypotrochoid in a plane.

E3. The method according to E1 or E2, wherein the image (I) is registered against the reference image (132) by calculating a Weighted Normalized Cross-correlation between the image and the reference image (132).

E4. The method according to any of E1 to E3, further comprising:

generating an updated reference image (132) by updating the reference image (132) to include the image data of the image that has been registered against the reference image (132).

E5. The method according to E4, wherein the image is registered against the reference image (132) by calculating a Weighted Normalized Cross-correlation between the image (I) and the reference image (132), and the updated reference image is generated on condition that a maximum of the calculated Weighted Normalized Cross-correlation between the image (I) and the reference image (132) exceeds a threshold.

E6. The method according to E5, wherein the threshold is a first threshold, and the image is registered against the reference image (132) by determining a translational difference between the image (I) and the reference image (132), and wherein the updated reference image (132) is generated on condition that the maximum of the calculated Weighted Normalized Cross-correlation between the image (I) and the reference image (132) exceeds the first threshold, and the determined translational difference exceeds a second threshold.

E7. The method according to any of E4 to E6, wherein the acquiring and mapping of the samples, the registering of the image (I) against the reference image (132), and the generating of the updated reference image (132) are performed in an iterative process, such that the image (I) defined by the image data generated by the optical imaging module (110) in each iteration of the iterative process is registered against, and subsequently used to update, the reference image (132) updated in a previous iteration of the iterative process.

E8. The method according to E7, wherein the optical imaging module (110) is controlled to generate image data defining a plurality of images (I) of different respective regions of the body part that are offset relative to one another by acquiring a plurality of sequences of the samples, wherein the pixels to which the samples of the acquired sequences of samples are mapped have pixel locations that follow a same path in each of the images (I).

E9. The method according to E7, wherein the optical imaging module (110) is controlled to generate image data defining a plurality of images (I) of the region of the body part by acquiring a plurality of sequences of the samples, wherein the pixels to which the samples of the acquired sequences of samples are mapped have pixel locations that follow a different path in each of the images (I).

E10. The method according to E9, further comprising:

keeping a record of a number of times each of a plurality of pixels of the reference image (132) has been updated during performance of the iterative process; and in each iteration of the iterative process, the method comprises:

calculating a respective degree of correlation between the record and each of a plurality of candidate imaging templates, wherein each candidate imaging template comprises a different predicted image of a candidate region of the body part to be imaged by the optical imaging module (110), the optical imaging module (110) being operable to generate, in accordance with each of the candidate imaging templates, image data defining an image of a respective candidate region of the body part by acquiring samples whose values are indicative of the optical property of the body part at respective sample locations in the candidate region, and mapping the acquired samples to corresponding pixels of the image such that the sample value and an indication of the sample location of each sample are mapped to a pixel value and a pixel location of a corresponding pixel of the image, wherein the optical imaging module (110) is configured to use the mapping to determine sample locations in the candidate imaging region at which the samples are to be acquired;

selecting, based on calculated degrees of correlation, a respective imaging template from the plurality of candidate imaging templates; controlling the optical imaging module (110) to generate image data using the selected imaging template;

registering, against the reference image (132), the image (I) defined by the image data that has been generated in accordance with the selected imaging template;

updating the reference image (132) to include the image data of the image that has been registered against the reference image (132); and updating the record using the image data of the image that has been registered against the reference image (132).

E11. The method according to E10, wherein, in each iteration, an imaging template is selected as the respective imaging template from the plurality of candidate imaging templates whose calculated degree of correlation with the record is between a highest of the calculated degrees of correlation and a lowest of the calculated degrees of correlation, and preferably a median of the calculated degrees of correlation.

In the foregoing description, example aspects are described with reference to several example embodiments. Accordingly, the specification should be regarded as illustrative. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g. program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A medical imaging device comprising:
an optical imaging module operable to generate image data defining an image of a region of a body part by acquiring samples whose values are indicative of an optical property of the body part at respective sample locations in the region, the samples being acquired by measuring an intensity of light that is or is based on light transmitted through the body part, or light that is or is based on light reflected from the imaged region of the body part, and using a mapping to map the acquired samples to corresponding pixels of the image such that an indication of the sample location of each sample is mapped to a pixel location of a corresponding pixel of the image;
a control module to control the optical imaging module to generate the image data by acquiring a first sequence of samples whose corresponding pixel locations in the image follow a path that is spanned by pixels corresponding to the first sequence of samples and extends over a greater portion of the image than an arrangement in an array of a sequence of pixels corresponding to a second sequence of samples that the optical imaging module is operable to acquire, wherein a sum of distances between adjacent pixels in the sequence of pixels is equal to a length of the path;
a registration module configured to register the image against a reference image comprising an image of a part of the region; and
an updating module configured to generate an updated reference image by updating the reference image to include the image data of the image that has been registered against the reference image.

2. The medical imaging device according to claim 1, wherein the control module is configured to determine the sample locations at which the optical imaging module acquires the samples in the first sequence based on a function which defines one of a spiral, an ellipse, an elliptical spiral, a Lissajous figure, and a hypotrochoid in a plane.

3. The medical imaging device according to claim 1, wherein the registration module is configured to register the image against the reference image by calculating a Weighted Normalized Cross-correlation between the image and the reference image.

4. The medical imaging device according to claim 1, wherein the registration module is configured to register the image against the reference image by calculating a Weighted Normalized Cross-correlation between the image and the reference image, and wherein the updating module is configured to generate the updated reference image provided that a maximum of the calculated Weighted Normalized Cross-correlation between the image and the reference image exceeds a threshold.

5. The medical imaging device according to claim 4, wherein the threshold is a first threshold, and the registration module is configured to register the image against the reference image by determining a translational difference between the image and the reference image, and wherein the updating module is configured to generate the updated reference image provided that the maximum of the calculated Weighted Normalized Cross-correlation between the image and the reference image exceeds the first threshold, and the translational determined difference exceeds a second threshold.

6. The medical imaging device according to claim 1, wherein the optical imaging module, the control module, the registration module and the updating module are configured to perform the acquiring and mapping of the samples, the registering of the image against the reference image, and the generating of the updated reference image in an iterative process, such that the image defined by the image data generated by the optical imaging module in each iteration of the iterative process is registered by the registration module against, and subsequently used by the updating module to update, the reference image updated in a previous iteration of the iterative process.

7. The medical imaging device according to claim 6, wherein the control module is configured to control the optical imaging module to generate image data defining a plurality of images of different respective regions of the body part that are offset relative to one another by acquiring a plurality of sequences of the samples, wherein the pixels to which the samples of the acquired sequences of samples are mapped have pixel locations that follow a same path in each of the images.

8. The medical imaging device according to claim 6, wherein the control module is configured to control the optical imaging module to generate image data defining a plurality of images of the region of the body part by acquiring a plurality of sequences of the samples, wherein the pixels to which the samples of the acquired sequences of samples are mapped have pixel locations that follow a different path in each of the images.

9. The medical imaging device according to claim 8, wherein:
the control module is configured to keep a record of a number of times each of a plurality of pixels of the reference image has been updated during performance of the iterative process; and in each iteration of the iterative process:
the control module is configured to calculate a respective degree of correlation between the record and each of a plurality of candidate imaging templates, wherein each candidate imaging template comprises a different predicted image of a candidate region of the body part to be imaged by the optical imaging module, the optical imaging module being operable to generate, in accordance with each of the candidate imaging templates, image data defining an image of a respective candidate region of the body part by acquiring samples whose values are indicative of the optical property of the body part at respective sample locations in the candidate region, and mapping the acquired samples to corresponding pixels of the image such that the sample value and an indication of the sample location of each sample are mapped to a pixel value and a pixel location of a corresponding pixel of the image, wherein the optical imaging module is configured to use the mapping to determine sample locations in the candidate imaging region at which the samples are to be acquired;
the control module is configured to select, based on calculated degrees of correlation, a respective imaging template from the plurality of candidate imaging templates;
the control module is configured to control the optical imaging module to generate image data using the selected imaging template;
the registration module is configured to register, against the reference image, the image defined by the image data that has been generated in accordance with the selected imaging template; and
the updating module is configured to:
update the reference image to include the image data of the image that has been registered against the reference image; and
update the record using the image data of the image that has been registered against the reference image.

10. The medical imaging device according to claim 9, wherein, in each of the iterations, the control module is configured to select, as the respective imaging template, an imaging template from the plurality of candidate imaging templates whose calculated degree of correlation with the record is between a highest of the calculated degrees of correlation and a lowest of the calculated degrees of correlation, and preferably a median of the calculated degrees of correlation.

11. The medical imaging device according to claim 1, wherein the medical imaging device is a retinal scanner for scanning a region of a retina of an eye, and wherein the optical imaging module is operable to generate image data defining an image of the region of the retina by acquiring samples whose values are indicative of the optical property of the retina at respective scan locations in the region.

12. The medical imaging device according to claim 11, wherein the retinal scanner comprises one of a scanning laser ophthalmoscope, SLO, an optical coherence tomography, OCT, scanner and a combined SLO-OCT scanner.

13. A method performed by a processor of a medical imaging device, comprising an optical imaging module which is operable to generate image data defining an image of a region of a body part by acquiring samples whose values are indicative of an optical property of the body part at respective sample locations in the region, the samples being acquired by measuring an intensity of light that is or is based on light transmitted through the body part, or light that is or is based on light reflected from the imaged region of the body part, and using a mapping to map the acquired samples to corresponding pixels of the image such that an indication of the sample location of each sample is mapped to a pixel location of a corresponding pixel of the image, the method comprising:
controlling the optical imaging module to generate the image data by acquiring a first sequence of samples whose corresponding pixel locations in the image follow a path that is spanned by pixels corresponding to the first sequence of samples and extends over a greater portion of the image than an arrangement in an array of a sequence of pixels corresponding to a second sequence of samples that the optical imaging module is operable to acquire, wherein a sum of distances between adjacent pixels in the sequence of pixels is equal to a length of the path;
registering the image against a reference image comprising an image of a part of the region; and
generating an updated reference image by updating the reference image to include the image data of the image that has been registered against the reference image.

14. A computer program which, when executed by a processor of a medical imaging device which further comprises an optical imaging module operable to generate image data defining an image of a region of a body part by acquiring samples whose values are indicative of an optical property of the body part at respective sample locations in the region, the samples being acquired by measuring an intensity of light that is or is based on light transmitted through the body part, or light that is or is based on light reflected from the imaged region of the body part, and mapping the acquired samples to corresponding pixels of the image such that an indication of the sample location of each sample is mapped to a pixel location of a corresponding pixel of the image, causes the processor to perform a method comprising:
controlling the optical imaging module to generate the image data by acquiring a first sequence of samples whose corresponding pixel locations in the image follow a path that is spanned by pixels corresponding to the first sequence of samples and extends over a greater portion of the image than an arrangement in an array of a sequence of pixels corresponding to a second sequence of samples that the optical imaging module is operable to acquire, wherein a sum of distances between adjacent pixels in the sequence of pixels is equal to a length of the path;
registering the image against a reference image comprising an image of a part of the region; and
generating an updated reference image by updating the reference image to include the image data of the image that has been registered against the reference image.

* * * * *